(12) United States Patent
Bougatef

(10) Patent No.: US 11,717,631 B2
(45) Date of Patent: Aug. 8, 2023

(54) VENTILATION SYSTEM WITH THREE-PORT VOLUME REGULATOR

(71) Applicant: Adel Bougatef, San Antonio, TX (US)

(72) Inventor: Adel Bougatef, San Antonio, TX (US)

( * ) Notice: Subject to any disclaimer, the term of this patent is extended or adjusted under 35 U.S.C. 154(b) by 337 days.

(21) Appl. No.: 17/089,345

(22) Filed: Nov. 4, 2020

(65) Prior Publication Data

US 2022/0134043 A1     May 5, 2022

(51) Int. Cl.
| | | |
|---|---|---|
| *A61M 16/08* | (2006.01) | |
| *A61M 16/00* | (2006.01) | |
| *A61M 16/16* | (2006.01) | |
| *A61M 16/20* | (2006.01) | |
| *A61M 16/22* | (2006.01) | |
| *A61M 39/24* | (2006.01) | |

(52) U.S. Cl.
CPC .... *A61M 16/0833* (2014.02); *A61M 16/0057* (2013.01); *A61M 16/0891* (2014.02); *A61M 16/16* (2013.01); *A61M 16/208* (2013.01); *A61M 16/22* (2013.01); *A61M 16/0066* (2013.01); *A61M 16/0875* (2013.01); *A61M 16/162* (2013.01); *A61M 16/209* (2014.02); *A61M 2039/244* (2013.01)

(58) Field of Classification Search
CPC .. A61M 16/00; A61M 16/0057; A61M 16/08; A61M 16/0816; A61M 16/0833; A61M 16/0866; A61M 16/0875; A61M 16/0883; A61M 16/0891; A61M 16/109; A61M 16/16; A61M 16/162; A61M 16/208; A61M 16/209; A61M 2039/244
See application file for complete search history.

(56) References Cited

U.S. PATENT DOCUMENTS

| | | | | |
|---|---|---|---|---|
| 4,807,616 A | * | 2/1989 | Adahan | ............ A61M 16/0069 417/44.1 |
| 5,007,420 A | | 4/1991 | Bird | |
| (Continued) | | | | |

FOREIGN PATENT DOCUMENTS

| | | | | |
|---|---|---|---|---|
| EP | 0262239 A1 | * | 4/1988 | ............ A61M 16/00 |
| WO | 2019243758 A1 | | 12/2019 | |

OTHER PUBLICATIONS

International Search Report and Written Opinion dated Mar. 4, 2022, from International Patent Application No. PCT/US2021/057522, 15 sheets.

*Primary Examiner* — Joseph D. Boecker
(74) *Attorney, Agent, or Firm* — Katten Muchin Rosenman LLP

(57) ABSTRACT

The disclosed invention provides a breathing circuit that includes a volume regulator that includes only three ports which include an inlet port connected to the exhalation port, a first outlet port connected to atmosphere, and a second outlet port connected to the moisturizer assembly. The breathing circuit is used for a ventilation system that delivers breaths to a patient. The inlet port of the volume regulator includes a flapper valve that moves only inward at an open position to receive the exhaled gas from the patient. The first outlet port includes a flapper valve that moves outward at an open position to exhaust gas in the volume regulator into the atmosphere. The second outlet port includes a flapper valve that moves only outward at an open position to exhaust gas in the volume regulator into the moisturizer assembly.

21 Claims, 5 Drawing Sheets

(56) References Cited

U.S. PATENT DOCUMENTS

| | | | |
|---|---|---|---|
| 5,121,746 A * | 6/1992 | Sikora | A61M 16/08 128/911 |
| 5,862,802 A | 1/1999 | Bird | |
| 7,849,853 B2 | 12/2010 | Grychowski et al. | |
| RE46,210 E * | 11/2016 | Dhuper | A61M 16/06 |
| 2003/0010344 A1* | 1/2003 | Bird | A61M 16/12 128/205.24 |
| 2007/0283958 A1 | 12/2007 | Naghavi | |
| 2009/0260628 A1* | 10/2009 | Flynn, Sr. | A61M 16/1065 128/203.29 |
| 2010/0249584 A1* | 9/2010 | Albertelli | A61M 16/0833 600/431 |
| 2013/0199520 A1* | 8/2013 | Dhuper | A61M 16/127 128/205.24 |
| 2016/0158477 A1 | 6/2016 | Dhuper | |
| 2021/0252236 A1* | 8/2021 | Khasawneh | A61M 16/0006 |

* cited by examiner

VENTILATION SYSTEM WITH THREE-PORT VOLUME REGULATOR

BACKGROUND

A ventilation system or ventilator is a machine that provides ventilation by moving breathable gas into and out of the lungs, to deliver breaths to a patient who is physically unable to breathe, or breathing insufficiently. Ventilators are chiefly used in intensive-care medicine, home care, and emergency medicine and in anesthesiology. The ventilator may consist of a compressible air reservoir or turbine, air and oxygen supplies, a set of valves and tubes, and a disposable or reusable breathing or patient circuit. The gas reservoir delivers room-air, or in most cases, an air/oxygen mixture to the patient. If a turbine is used, the turbine pushes breathable gas through the ventilator, with a flow valve adjusting pressure to meet patient-specific parameters. When over pressure is released, the patient will exhale, and the exhaled gas from the patient is released through a one-way valve within the breathing circuit.

The breathing circuit includes a shuttle chamber that delivers the optimal volume and pressure of air/oxygen mixture to the patient, and a set of valves and tubes, and a volume regulator that controls volume of exhaled gas from the patient. The volume regulator is connected to atmosphere and allows the patient's exhaled gas, which is rich in carbon dioxide gas ($CO_2$), to escape to ambient or to recirculate within the inspiratory breathing circuit if needed.

The conventional volume regulator has an outlet at which a balloon or reservoir bag is connected. The balloon or reservoir bag serves as a reservoir for the patient's exhaled gas from the expiratory circuit. In the conventional volume regulator, the reservoir bag is provided to support an increase of ventilation rate, though there is a partial rebreathing of the exhaled gas from the patient. The reservoir bag is also provided for protection against inspiratory failure, expiratory failure, or gas source failure. The exhaled gas stored in the reservoir bag may be supplied to the patient in these failures. However, the balloon or reservoir bag attached to the conventional volume regulator also has problems. For example, The reservoir bag can inadvertently serve as a collection site for condensation. If the reservoir bag disconnects due to the weight of the condensation, it leaves the outlet open to ambient, and gas is entrained which alters the predetermined concentration of materials such as fraction of inspired oxygen ($FiO_2$), which needs to be delivered to the patient. For another example, when the conventional volume regulator is used for patients with virus infections such as Covid-19, the reservoir bag may work as a collector of the viruses. The presence of the reservoir bag filled with exhaled gas coming from the patient, which is rich with viruses, will increase the risk of contamination for overall ventilation system and also the environment near the patient.

SUMMARY

In order to overcome the disadvantages and issues of the conventional volume regulator, the disclosed invention provides a ventilation system including a volume regulator that does not require the reservoir bag described above. The volume regulator of the disclosed invention is purposely designed without the reservoir bag of the conventional volume regulator, and as such reduces the rebreathing of excess carbon dioxide ($CO_2$) and maintains the desired concentration of materials such as $FiO_2$ delivered to the patient. The change in design will not affect the ventilator performance nor patient safety.

These advantages and others are achieved, for example, by an A ventilation system for delivering breaths to a patient. The ventilation system includes a shuttle chamber configured to supply inhalation gas to the patient and to receive exhaled gas from the patient, a volume regulator coupled to the exhalation port of the shuttle chamber, and a moisturizer assembly coupled to the volume regulator. The shuttle chamber includes an exhalation port to which the exhaled gas from the patient is directed. The volume regulator includes only three ports which are an inlet port connected to the exhalation port, a first outlet port connected to atmosphere, and a second outlet port connected to the moisturizer assembly.

The first outlet port may be formed to face the inlet port, and the second outlet port may be formed to be substantially perpendicular to a line between the first outlet port and the inlet port. Sizes of the inlet port, first outlet port and second outlet port may be different from each other. The inlet port of the volume regulator may include a flapper valve that moves only inward at an open position to receive the exhaled gas from the patient. The first outlet port of the volume regulator may include a flapper valve that moves outward at an open position to exhaust gas in the volume regulator into the atmosphere. The second outlet port the volume regulator may include a flapper valve that moves only outward at an open position to exhaust gas in the volume regulator into the moisturizer assembly.

The ventilation system may further include a ventilator that supplies gases to the shuttle chamber and to the moisturizer assembly. The moisturizer assembly may include an enclosure connected to the second outlet of the volume regulator, and a moisturizer bowl connected to the moisturizer enclosure to add moisture to the gas supplied from the ventilator. The ventilation system may include sterile water reservoir to supply sterile water the moisturizer bowl. The ventilation system may include an external heater and humidifier connected to the moisturizer assembly and the shuttle chamber. The external heater and humidifier receives gas from the moisturizer assembly and delivers humidified and heated gas to the shuttle chamber. The ventilation system may include an inhalation safety valve assembly connected between the inlet port of the volume regulator and the exhalation port of the shuttle chamber. The inhalation safety valve assembly may include an inhalation safety valve that is connected to the atmosphere and allows gas flow only in a direction into an inside of the inhalation safety valve assembly from the atmosphere. The inhalation safety valve may include a flapper valve that moves only inward at an open position to draw air from the atmosphere.

These advantages and others are also achieved, for example, by a breathing circuit for a ventilation system that delivers breaths to a patient. The breathing circuit includes a shuttle chamber configured to supply inhalation gas to the patient and to receive exhaled gas from the patient, a volume regulator coupled to the exhalation port of the shuttle chamber, and a moisturizer assembly coupled to the volume regulator. The shuttle chamber includes an exhalation port to which the exhaled gas from the patient is directed. The volume regulator includes only three ports which comprises an inlet port connected to the exhalation port, a first outlet port connected to atmosphere, and a second outlet port connected to the moisturizer assembly.

These advantages and others are also achieved, for example, by a volume regulator for a ventilation system that delivers breaths to a patient. The volume regulator includes only three ports which include an inlet port to receive exhaled gas from the patient, a first outlet port coupled to atmosphere, and a second outlet port coupled to a moisturizer assembly to supply gas to the moisturizer assembly if needed. The inlet port is coupled to a shuttle chamber of the ventilation system, and the shuttle chamber is configured to supply inhalation gas to the patient and to receive the exhaled gas from the patient. The inlet port includes a flapper valve that moves only inward at an open position to receive the exhaled gas from the patient.

BRIEF DESCRIPTION OF THE DRAWINGS

The preferred embodiments described herein and illustrated by the drawings hereinafter be to illustrate and not to limit the invention, where like designations denote like elements.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
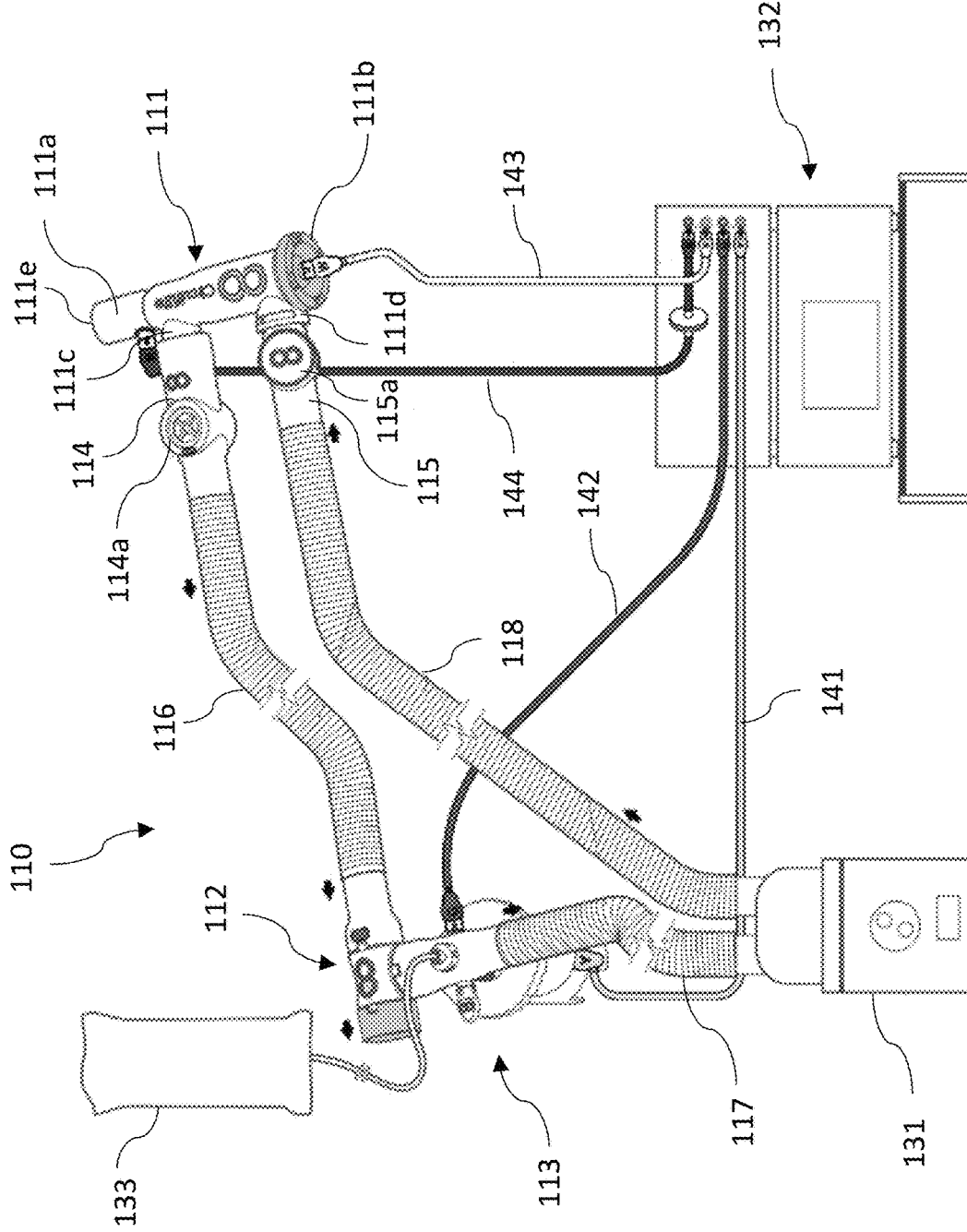
FIG. 1 is a diagram illustrating ventilation system of the disclosed invention.
Figure 2:
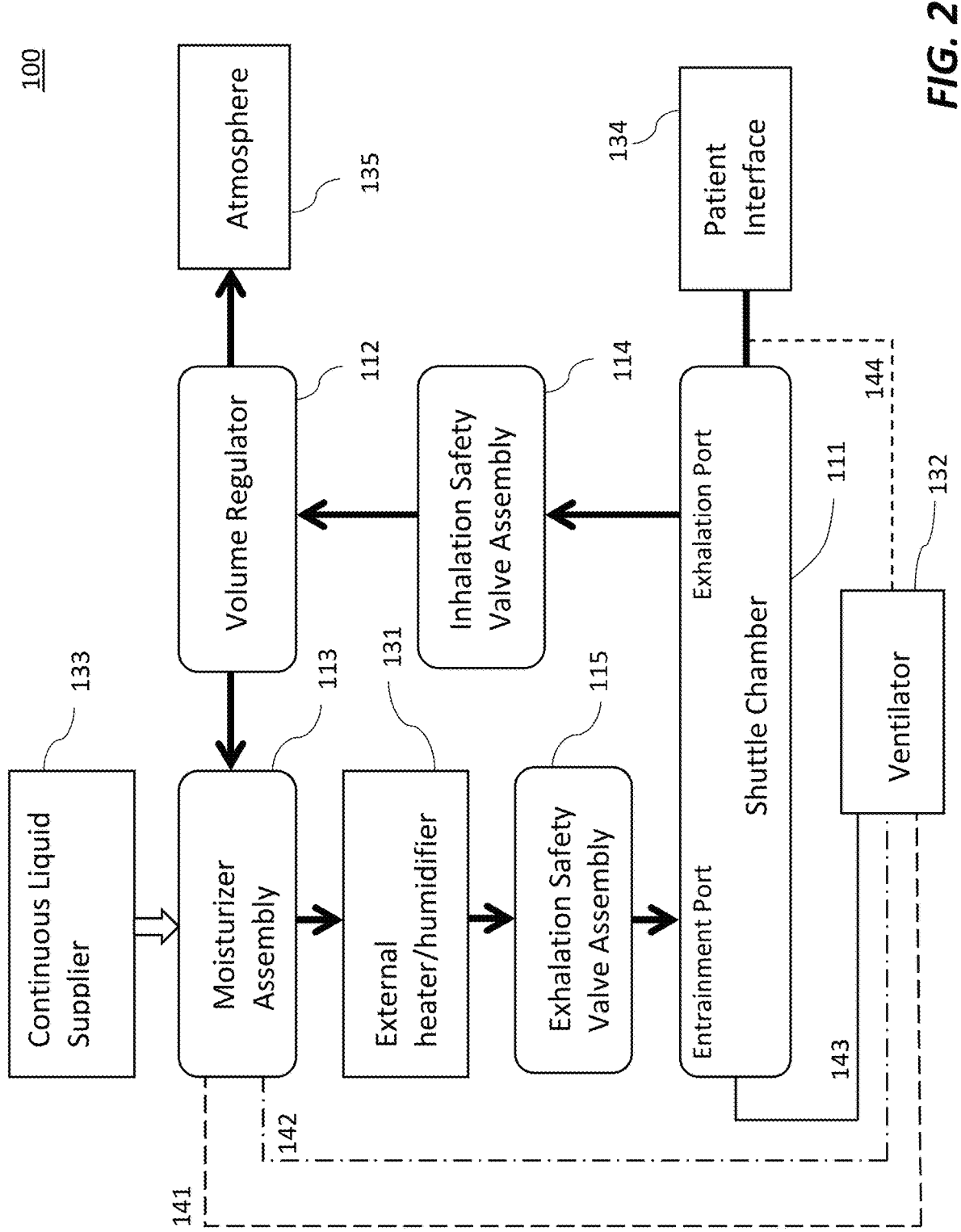
FIG. 2 is a simplified block diagram architecture of the ventilation system of the disclosed invention.

With reference to FIG. 1, shown is a diagram for ventilation system 100 of the disclosed invention. With reference to FIG. 2, shown is a simplified block diagram architecture of the ventilation system 100 of the disclosed invention. Ventilation system 100 includes breathing circuit 110 that includes shuttle chamber 111, inhalation safety valve assembly 114 connected to exhalation port 111c of the shuttle chamber 111, volume regulator 112 connected to the inhalation safety valve assembly 114, moisturizer assembly 113 connected to the volume regulator 112, and exhalation safety valve assembly 115 connected to entrainment port 111d of the shuttle chamber 111. The breathing circuit 110 may further include exhalation tube 116 connected between the inhalation safety valve assembly 114 and the volume regulator 112, first bias tube 117 connected to downstream side of the moisturizer assembly 113, and second bias tube 118 connected to upstream side of the shuttle chamber 111. In FIG. 2, elements in round rectangles represent the elements of the breathing circuit 110.

The ventilation system 100 further includes external heater/humidifier 131 connected to the moisturizer assembly 113 through the first bias tube 117, sterile water reservoir 133 connected to moisturizer assembly 113 to supply sterile water, and ventilator 132 coupled to the breathing circuit 110 to supply gases to shuttle chamber 111 and moisturizer assembly 113. The external heater/humidifier 131 is connected to the exhalation safety valve assembly 115 to supply heated and humidified gas to the shuttle chamber 111. The ventilator 132 supplies first gas to bowl 302 (see FIG. 4A) of the moisturizer assembly 113 through first small bore tube 141 (generally in yellow color), second gas to the enclosure 301 (see FIG. 4A) of the moisturizer assembly 113 through second small bore tube 142 (generally in green color), and third gas to the rear end 111b of the shuttle chamber 111 through third small bore tube 143 (generally in white color). Ventilator 132 may supply air/oxygen (02) mixture to the rear end 111b of the shuttle chamber 111 through the third small bore tube 143. This oxygen gas may be supplied in a form of a pulsed gas stream. The ventilator 132 may supply air/oxygen gas to the enclosure 301 through the second small bore tube 142, and this air/oxygen gas may be supplied in a pulsed gas stream that is out of phase with the pulsed oxygen gas supplied through the third small bore tube 143. The ventilator 132 may supply air/oxygen gas to a bottom side of the bowl 302 through the first small bore tube 141 to provide a constant aerosolization to the patient. Fourth small bore tube 144 (generally in red color) is connected to front end 111a of the shuttle chamber 111 to detect pressure of gas at the front end 111a. Gas sample from the front end 111a may be delivered to the ventilator 132 to measure the pressure.

Referring to FIG. 1, the shuttle chamber 111 has a exhalation port 111c near the front end 111a of the shuttle chamber 111, and has entrainment port 111d near the rear end 111b of the shuttle chamber 111. The inhalation safety valve assembly 114 is connected to an exhalation port 111c, and the exhalation safety valve assembly 115 is connected to an entrainment port 111d of the shuttle chamber 111. The shuttle chamber 111 controls airflow into and out of a patient to deliver breaths to the patient. In a normal operation, the patient inhales air/oxygen gas supplied by the shuttle chamber 111. When the patient exhales, the exhaled gas from the patient is directed to the exhalation port 111c. The front end 111a has a patient interface port 111e, and patient interface 134 such as a mouthpiece is coupled to the patient interface port 111e of the shuttle chamber 111 to supply gas to lungs of the patient and receive gas exhaled from the lungs of the patient. The shuttle chamber 111 may include a Venturi tube to control airflow and pressure.

Figures 3A, 3B:
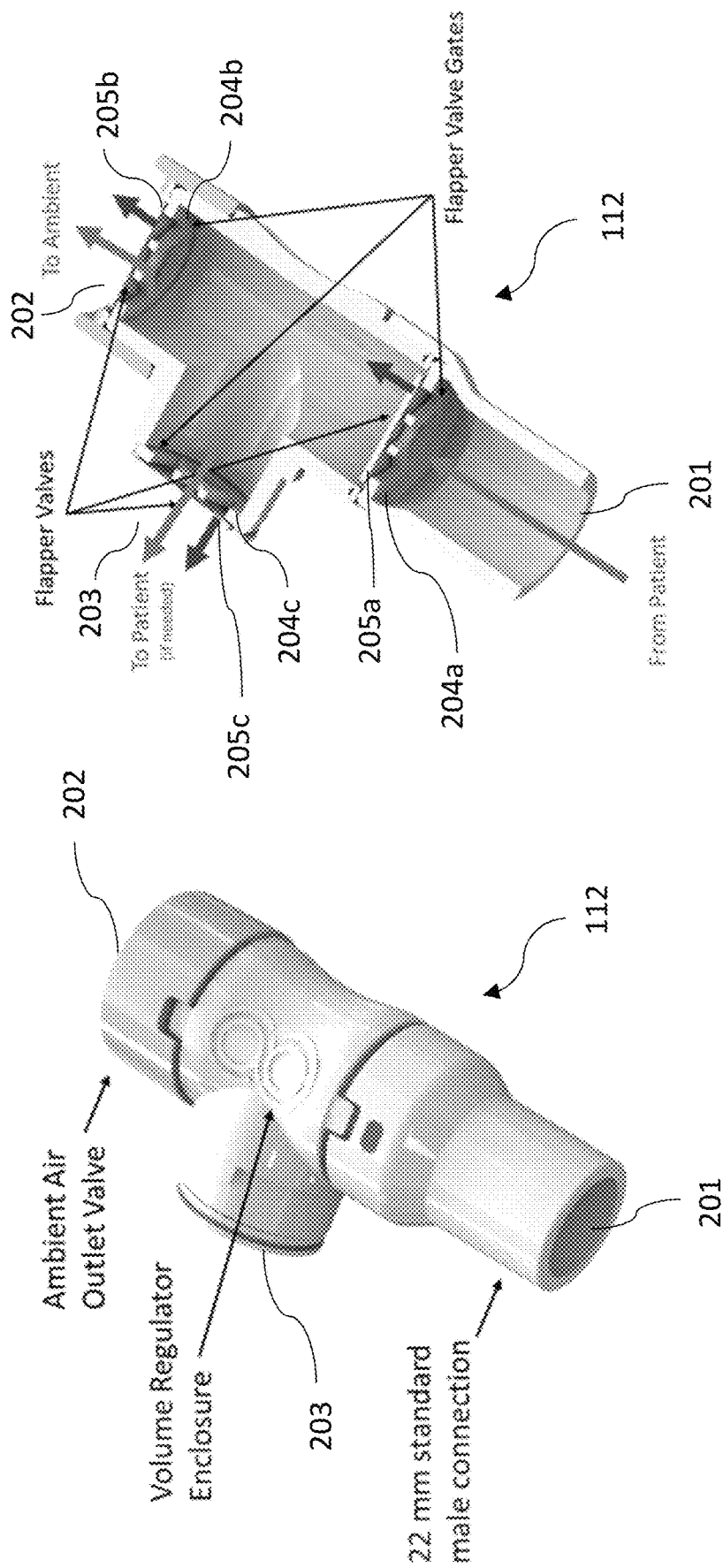
FIGS. 3A-3B are perspective views of exterior structures and interior structures of volume regulator of the disclosed invention.
Figure 4B:
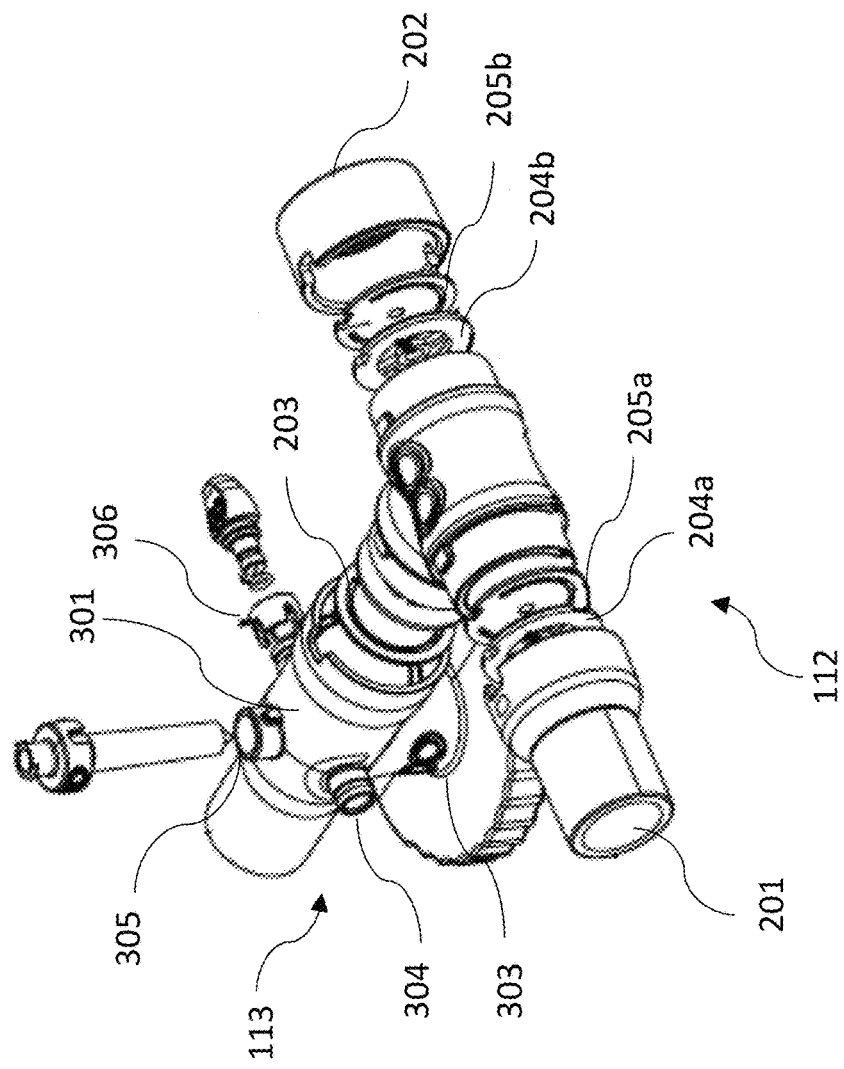
FIGS. 4A-4B are perspective views of the volume regulator connected with moisturizer assembly.
Figure 4A:
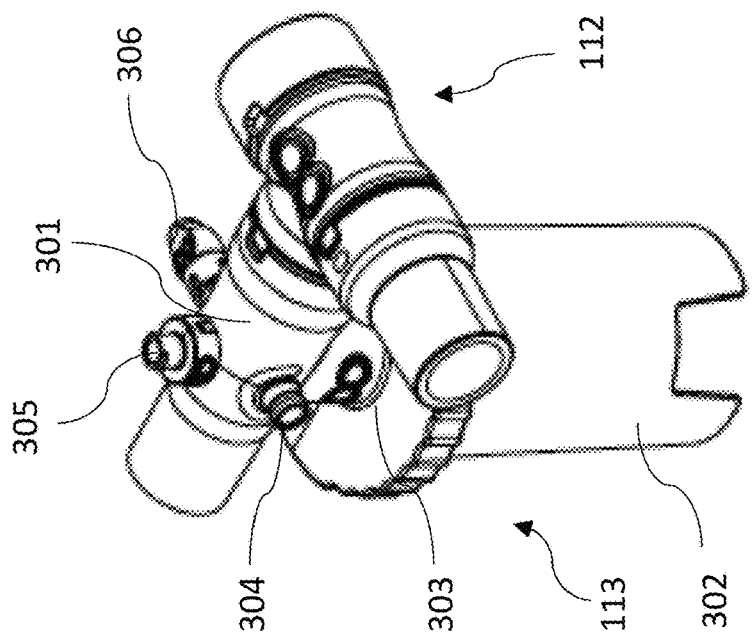

With reference to FIGS. 3A-3B, shown are perspective views of exterior structures and interior structures of volume regulator 112 of the disclosed invention. With reference to FIGS. 4A-4B, shown are perspective views of volume regulator 112 connected with moisturizer assembly 113 of the disclosed invention. The volume regulator 112 of the disclosed invention has only three ports which include inlet port 201, first outlet port 202, and second outlet port 203. The volume regulator 112 of the disclosed invention does not require an additional port than the three ports. The inlet port 201 is connected to the inhalation safety valve assembly 114 to receive exhaled gas from the patient. The first outlet port 202 is connected to atmosphere to exhaust the exhaled gas from the patient to ambient environment. The second outlet port 203 is connected to the moisturizer assembly 113 to supply a portion of the exhaled gas to the moisturizer assembly 113 if needed.

The volume regulator 112 includes flapper valves mounted on flapper valve gates at inlet port 201, first outlet port 202, and second outlet port 203. As shown in FIGS. 3B and 4B, inlet flapper valve gate 204a is placed at the inlet port 201, and inlet flapper valve 205a is mounted at an inner side (toward inside of the volume regulator 112) of the inlet flapper valve gate 204a. The inner flapper valve 205a is constructed only to move to inward direction (at an open position) to receive gas from the inhalation safety valve assembly 114. The inner flapper valve 205a is not allowed to move outward to exhaust gas in the volume regulator 112 to the inhalation safety valve assembly 114. Gas inside the volume regulator 112 cannot escape in the direction to the inhalation safety valve assembly 114 through the flapper valve 205a.

First outlet flapper valve gate 204b is placed at the first outlet port 202, and first outlet flapper valve 205b is mounted at an outer side (opposite to the inner side of the volume regulator 112) of the first outlet flapper valve gate 204b. The first outlet flapper valve 205b may be constructed only to move to outward direction (at an open position) into atmosphere to exhaust gas in the volume regulator 112.

Second outlet flapper valve gate 204c is placed at the second outlet port 203, and second outlet flapper valve 205c is mounted at an outer side (opposite to the inner side of the volume regulator 112) of the second outlet flapper valve gate 204c. The second outlet flapper valve 205c is constructed only to move to outward direction (at an open position) into the moisturizer assembly 113 to exhaust gas in the volume regulator 112 to the moisturizer assembly 113 if needed. The second outlet flapper valve 205c is not allowed to move inward to draw gas from the moisturizer assembly 113 into the volume regulator 112. In other words, gas from the moisturizer assembly 113 cannot flow into the volume regulator 112 through the flapper valve 205c.

In an embodiment, as shown in FIGS. 3A-3B, the first outlet port 202 is formed to straight face the inlet port 201, and the second outlet port 203 is formed to be substantially perpendicular to a line between the first outlet port 202 and the inlet port 201. In this configuration, the exhaled gas from the patient, which is received through the inlet port 201, may be easily exhausted to the first outlet port 202. Cross-sections of the inlet port 201, first outlet port 202 and second outlet port 203 may have circular shapes, and have difference sizes or diameters to prevent misconnections. For example, the inlet port 201 may have 22 mm standard male connection, and the size of the male connector of the inlet port 201 may not fit to the enclosure 301 of the moisturizer assembly 113. The size (or diameter) of first outlet port 202 may be larger than the size of inlet port 201 so that the exhalation tube 116 may not fit to the first outlet port 202. In order to prevent misconnections, a marking such as a purple sticker may be placed on top of the inlet port 201 of the volume regulator 112 to facilitate usability of connection to the inhalation safety valve assembly 114. In the case of Covid-19 or other virus infections, anti-viral filter may be connected to the inlet port 201 of the volume regulator 112.

Referring to FIGS. 4A-4B, the moisturizer assembly 113 includes enclosure 301 and moisturizer bowl 302. An end of the enclosure 301 is connected to the second outlet port 203 of the volume regulator 112, and receives gas, if needed, from the volume regulator 112. For example, when inadequate flow is supplied to the shuttle chamber 111 due to malfunction of the ventilator 132 or when the first small bore tube 141 (yellow line) stops functioning, the flapper valve 205c may move toward the enclosure 301 (open position) to be opened and gas in the volume regulator 112 may flow into the enclosure 310 through the open flapper valve 205c. In other word, the volume regulator 112 will instantaneously manage the exhaled gas flow by directing it to ambient in normal use, or to the inspiratory part of the breathing circuit 110, if for any reason the ventilation system 100 experiences drop in bias flow.

The moisturizer bowl 302 adds moisture to gas supplied through the first small bore tube 141 connected at the bottom of the bowl 302. The moisturized gas is supplied to the external heater/humidifier 131 through the first bias tube 117. The enclosure 301 has port 303 connected to the moisturizer bowl 302, and gas port 304 connected to the second small bore tune 142 to receive air/oxygen from the ventilator 132. Additionally, the enclosure 301 has water port 305 that is connected to sterile water reservoir 133 that supplies sterile water to the bowl 302 of the moisturizer assembly 113. The enclosure 301 also has an additional port 306 through which additional gas or medicine, which is needed for the patient, is provided to the ventilation system 100.

Figure 5A:
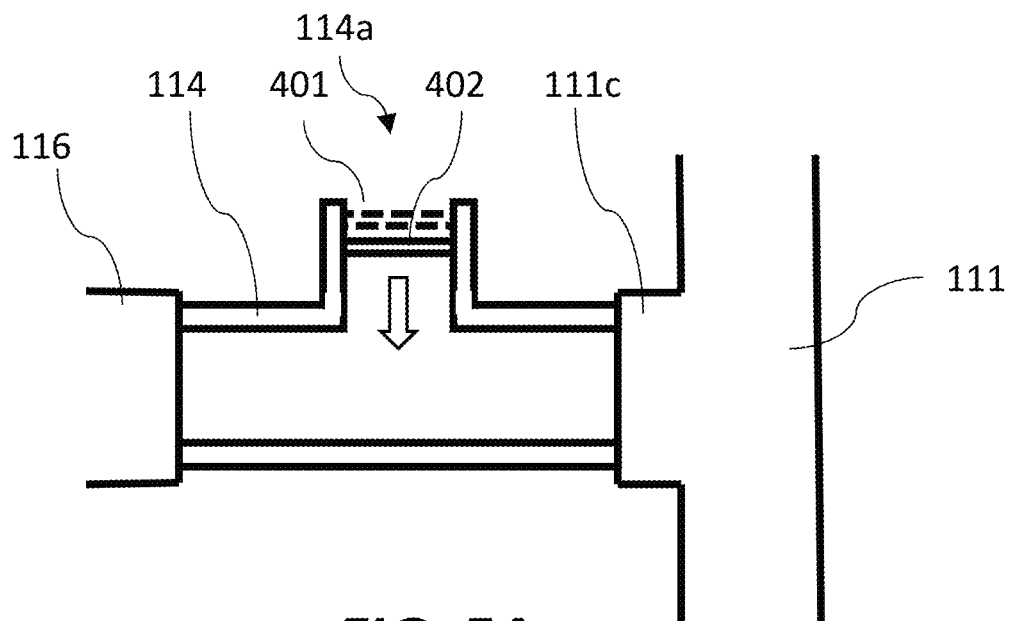
FIGS. 5A-5B are cross-sectional views of inhalation safety valve assembly and exhalation safety valve assembly, respectively.
Figure 5B:
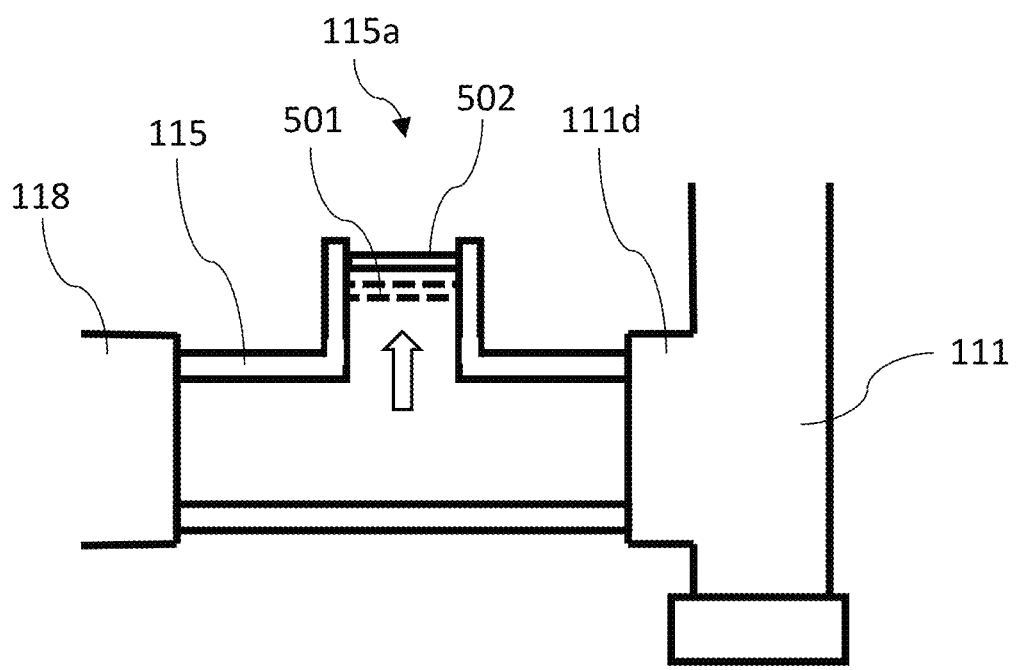

With reference to FIGS. 5A-5B, shown are cross-sectional views of inhalation safety valve assembly 114 and exhalation safety valve assembly 115, respectively. As shown in FIGS. 1 and 2, the inhalation safety valve assembly 114 has inhalation safety valve 114a, and the exhalation safety valve assembly 115 has exhalation safety valve 115a.

Referring to FIG. 5A, the inhalation safety valve 114a is configured to only to draw gas inward (toward the interior of the assembly 114) so that the valve 114a can admit ambient air, if needed, into the assembly 114. Gas inside the assembly 114 cannot flow out through the valve 114a. For example, the inhalation safety valve 114a may have valve gate 401 and flapper valve 402 placed inward side of the valve gate 401. The flapper valve 402 moves inward at an open position to admit ambient air if pressure inside the assembly 114 is lower than ambient pressure. The inhalation safety valve 114a is provided for safety purpose. For example, if the ventilator 132 is turned off or an gas tube such as the first small bore tube 141 is disconnected, no sufficient gas may be supplied to the patient. In this situation, when the patient inhales, the flapper valve 402 moves inward at an open position due to lower pressure inside the assembly 114 and admits ambient air, and the patient still be able to breathe the air supplied from the open flapper valve 402. In normal operation, the flapper valve 402 remains at a closed position.

Referring to FIG. 5B, the exhalation safety valve 115a is configured to exhaust gas outward to atmosphere. For example, the exhalation safety valve 115a may have valve gate 501 and flapper valve 502 placed outward side of the valve gate 501. The flapper valve 502 moves outward to atmosphere at an open position. The exhalation safety valve 115a is also provided for safety purpose. For example, if for some reasons, pressure is build up inside the shuttle chamber 111, the patient may not be able properly exhale due to the higher pressure inside the shuttle chamber 111. In this situation, the flapper valve 502 may be pushed to move to be open to atmosphere, due to higher pressure around the entrainment port 111d. Entrained gas from the second bias tube 118 may partially escape through the exhalation safety valve 115a.

Since many modifications, variations, and changes in detail can be made to the described preferred embodiments of the invention, it is intended that all matters in the foregoing description and shown in the accompanying drawings be interpreted as illustrative and not in a limiting sense. Consequently, the scope of the invention should be determined by the appended claims and their legal equivalents.

What is claimed is:

1. A ventilation system for delivering breaths to a patient, comprising:
   a shuttle chamber configured to supply inhalation gas to the patient and to receive exhaled gas from the patient, wherein the shuttle chamber comprises an exhalation port to which the exhaled gas from the patient is directed;
   a volume regulator coupled to the exhalation port of the shuttle chamber;
   a moisturizer coupled to the volume regulator, wherein the volume regulator comprises only three ports which comprises an inlet port connected to the exhalation port, a first outlet port connected to atmosphere, and a second outlet port connected to the moisturizer; and
   a ventilator configured to supply gases to the shuttle chamber and to the moisturizer.

2. The ventilation system of claim 1 wherein the first outlet port is formed to face the inlet port, and the second outlet port is formed to be substantially perpendicular to a line between the first outlet port and the inlet port.

3. The ventilation system of claim 1 wherein sizes of the inlet port, first outlet port and second outlet port are different from each other.

4. The ventilation system of claim 1 wherein the inlet port of the volume regulator includes a flapper valve that moves only inward at an open position to receive the exhaled gas from the patient.

5. The ventilation system of claim 1 wherein the first outlet port of the volume regulator includes a flapper valve that moves outward at an open position to exhaust gas in the volume regulator into the atmosphere.

6. The ventilation system of claim 1 wherein the second outlet port the volume regulator includes a flapper valve that moves only outward at an open position to exhaust gas in the volume regulator into the moisturizer.

7. The ventilation system of claim 1 wherein the moisturizer comprises:
   an enclosure connected to the second outlet of the volume regulator; and
   a moisturizer bowl connected to the moisturizer enclosure to add moisture to the gas supplied from the ventilator.

8. The ventilation system of claim 7 further comprising a sterile water reservoir to supply sterile water to the moisturizer bowl.

9. The ventilation system of claim 7 further comprising an external heater and humidifier connected to the moisturizer and the shuttle chamber, wherein the external heater and humidifier receives gas from the moisturizer and delivers humidified and heated gas to the shuttle chamber.

10. The ventilation system of claim 1 further comprising an inhalation safety valve assembly connected between the inlet port of the volume regulator and the exhalation port of the shuttle chamber, wherein the inhalation safety valve assembly includes an inhalation safety valve that is connected to the atmosphere and allows gas flow only in a direction into an inside of the inhalation safety valve assembly from the atmosphere.

11. The ventilation system of claim 10 wherein the inhalation safety valve includes a flapper valve that moves only inward at an open position to draw air from the atmosphere.

12. A breathing circuit for a ventilation system that delivers breaths to a patient, comprising:
   a shuttle chamber configured to supply inhalation gas to the patient and to receive exhaled gas from the patient, wherein the shuttle chamber comprises an exhalation port to which the exhaled gas from the patient is directed;
   a volume regulator coupled to the exhalation port of the shuttle chamber; and
   a moisturizer coupled to the volume regulator, wherein the volume regulator comprises only three ports which comprises an inlet port connected to the exhalation port, a first outlet port connected to atmosphere, and a second outlet port connected to the moisturizer.

13. The breathing circuit of claim 12 wherein the first outlet port is formed to face the inlet port, and the second outlet port is formed to be substantially perpendicular to a line between the first outlet port and the inlet port.

14. The breathing circuit of claim 12 wherein sizes of the inlet port, first outlet port and second outlet port are different from each other.

15. The breathing circuit of claim 12 wherein the inlet port of the volume regulator includes a flapper valve that moves only inward at an open position to receive the exhaled gas from the patient.

16. The breathing circuit of claim 12 wherein the first outlet port of the volume regulator includes a flapper valve that moves outward at an open position to exhaust gas in the volume regulator into the atmosphere.

17. The breathing circuit of claim 12 wherein the second outlet port the volume regulator includes a flapper valve that moves only outward at an open position to exhaust gas in the volume regulator into the moisturizer.

18. A volume regulator for a ventilation system that delivers breaths to a patient, comprising only three ports which comprises:
   an inlet port to receive exhaled gas from the patient, wherein the inlet port is configured to be coupled to a shuttle chamber of the ventilation system which is configured to supply inhalation gas to the patient and to receive the exhaled gas from the patient, and wherein the inlet port includes a flapper valve that moves only inward at an open position to receive the exhaled gas from the patient;
   a first outlet port coupled to atmosphere; and
   a second outlet port configured to be coupled to a moisturizer and configured to supply gas to the moisturizer.

19. The volume regulator of claim 18 wherein the second outlet port includes a flapper valve that moves only outward at an open position to exhaust gas in the volume regulator into the moisturizer.

20. The volume regulator of claim 18 wherein the first outlet port is formed to face the inlet port, and the second outlet port is formed to be substantially perpendicular to a line between the first outlet port and the inlet port.

21. The volume regulator of claim 18 wherein sizes of the inlet port, first outlet port and second outlet port are different from each other.

\* \* \* \* \*